United States Patent [19]

Barry et al.

[11] Patent Number: 5,991,729
[45] Date of Patent: Nov. 23, 1999

[54] METHODS FOR GENERATING PATIENT-SPECIFIC MEDICAL REPORTS

[76] Inventors: James T. Barry, 161 Wildwood Ave., Madison, Conn. 06443; Karen J. Casey, 52 Old Point Td., Milford, Conn. 06460; Mary Lachman, 3 Glenwood Crt., Bethany, Conn. 06524; David G. McGinnis, 44 Cathy Dr., Southington, Conn. 06497; Carl Niedmann, 2 Collin Ct., Wallingford, Conn. 06492; Vito Santarsieri, 247 North St., Manhasset Hills, N.Y. 11040; Michael Serra, 80 Blamey Cir., Stratford, Conn. 06497; Steven M. Tenner, 45 Lilac Ave., Hamden, Conn. 06517; William M. Tilton, 12 Baldwin St., West Haven, Conn. 06516

[21] Appl. No.: 08/896,314

[22] Filed: Jun. 28, 1997

[51] Int. Cl.$^6$ .................................................. G06F 17/60
[52] U.S. Cl. ......................................... 705/3; 705/2
[58] Field of Search .............................. 705/3, 2

[56] References Cited

U.S. PATENT DOCUMENTS

| 4,315,309 | 2/1982 | Coli ............................................. 705/3 |
| 5,581,460 | 12/1996 | Kotake et al. .............................. 705/3 |

*Primary Examiner*—Allen R. MacDonald
*Assistant Examiner*—Penny Caudle
*Attorney, Agent, or Firm*—Brian D. Voyce

[57] ABSTRACT

The present invention relates to novel methods and memory storage devices for generating a report that contains medical counseling information which is specific to a patient. The medical information is dependent upon the diagnostic analysis of a biological sample from the patient. A relational database management system is used that stores a plurality of diagnostic codes and archived textual and graphical information specific for each diagnostic code. By inputting a diagnostic code specific for the results of the diagnostic analysis, a report is compiled from retrieved archived textual and graphical information specific for the entered diagnostic code. The archived information provides counseling and descriptive information useful for the patient.

8 Claims, 2 Drawing Sheets

METHODS FOR GENERATING PATIENT-SPECIFIC MEDICAL REPORTS

TECHNICAL FIELD

The present invention relates to novel methods and memory storage devices for generating a report that contains medical counseling information which is specific to a patient. The medical information is dependent upon the diagnostic analysis of a biological sample from the patient. A relational database management system is used that stores a plurality of diagnostic codes and archived textual and graphical information specific for each diagnostic code. By inputting a diagnostic code specific for the results of the diagnostic analysis, a report is compiled from retrieved archived textual and graphical information specific for the entered diagnostic code. The archived information provides counseling and descriptive information useful for the patient.

BACKGROUND ART

The use of information processing systems in managing medical care has become increasingly important to both the patient and the physician. Computer software systems have been developed that enable for-profit health care enterprises to deny a patient access to medical care. U.S. Pat. No. 5,471,382 to Joseph P. Tallman et alia discloses a medical network management system based upon a patient assessment program that is stored on a computer system. The patient is asked questions generated by the program which have "yes" or "no" answers. First the patient's eligibility is checked. If eligible, then a series of questions is asked, the answers to which cause a particular branched chain algorithm to be selected. Once all the questions from the branched chain algorithm are answered, the number and type of questions being dependent upon particular answers to particular questions, a pre-selected analysis of the medical care to be offered the patient, if any, is generated, including the timing, type, and level of medical care.

Databases can store enormous amounts of patient information, and thus, expand the capabilities of physicians in making decisions. One way databases have been used to aid physicians in making a diagnosis is to transform data based on prior results of other patients. U.S. Pat. No. 5,594,637 to Alan J. Eisenberg et alia discloses transforming a physiological test result by using at least one non-test variable. The transformed test data is compared to the mean and standard deviation of a database of similarly transformed data. The likelihood of a given outcome for the patient is given. Simultaneously, the database is updated with the result from the new patient.

Relational databases have added physicians getting access to medical information. A use for relational databases in managing medical care is disclosed in U.S. Pat. No. 5,626,144 to Christopher A. Tacklind et alia. A system for monitoring and reporting medical measurements includes a stand-alone monitor that can store data records such as measured values and time stamps. The monitor transmits the records to a remote reporting unit over a communication system. When the reports are received by the remote reporting unit, they are entered into a relational database. Chronological graphs are generated for that patient of the measured values and transmitted to the health care provider.

Relational databases have been used to perform automatically prioritized nursing diagnoses based upon incoming patient assessment data. U.S. Pat. No. 5,404,292 to Maria F. Hendrickson discloses a data processing system that stores relations between patient characteristics and nursing diagnoses are stored in a relational database as primary and secondary diagnoses tables. The database also stores a priority table that links a particular diagnosis from the diagnoses tables with a corresponding measure of priority. A potential diagnosis list is generated from the patient assessment data. Each diagnosis is weighted from the accompanying priority measures in the priority table. Probability measures are added together from all diagnoses stemming from the total patient assessment data for a patient if more than one relation is provided for a diagnosis.

DISCLOSURE OF THE INVENTION

The present invention relates to a method that employs relational database software, operating on a computer system, to generate a document or report that contains various types of patient-specific archived medical information. The relational database management system is stored on a memory device and is executable for query and report compilation on a computer system, preferably a client/server environment. A diagnosis made as a result of analyzing a biological sample from the patient directs the exact medical information that is incorporated into the report.

Identification and archival information is entered into the relational database before a patient sample is analyzed. First, one assigns a unique identifier code for to each of a plurality of medical diagnoses, preferably each possible medical diagnosis, that can be made from the analysis of the biological samples to be examined. The diagnostic identifier code can be any alphanumeric sequence either assigned manually or generated randomly by an algorithm. Second, each diagnostic identifier code is entered into the relational database as an attribute for a medical diagnosis. Third, archival textual and graphic diagnostic information is entered into the relational database management system as an attribute that is specific for each diagnostic identifier code. This information aids the physician or patient in understanding the diagnosis, the basis for the diagnosis, the underlying medical condition or disease, and provides counseling that should be offered a patient in meeting a standard of care for a diagnosis. Fourth, one assigns a unique identifier code for a physician for the patient. The physician identifier code can be any alphanumeric sequence either assigned manually or randomly generated by an algorithm using a computer. Fifth, one enters the physician identifier code into the relational database management system as an attribute of the name and address of the physician.

The relational database is configured such that if a diagnostic identifier code is entered as an attribute for an entered patient identifier code, then a report can be compiled that retrieves and inserts the diagnostic archived textual and graphical information specific for the entered diagnostic code, identifies the patient, discloses the results of the sample analysis, and, preferably, addresses the report to the physician. Commercially available relational database software programs contain a programming means for producing such a compilation. The actual programming can be done by one of ordinary skill in the art.

The biological sample from the patient is analyzed using conventional techniques, which include histological tests, serological tests, or visual observations by a pathologist. A diagnosis is made as a result of the analysis, the diagnosis having an identifier code that has been entered into the relational database.

Either before or after the biological sample is analyzed, one assigns a unique identifier code for the patient. The patient identifier code can be any alphanumeric sequence either assigned manually or randomly generated by an algorithm. The patient identifier sequence is entered into the relational database management system as an attribute of the name of the patient.

In order to generate the patient-specific informational report, the diagnostic identifier code for the diagnosis is entered into the relational database management system along with the results of the sample analysis. A query for a report is made. The query can be made either manually or initiated as a result of the physician code, the patient code and the diagnostic code for a particular patient sample having been entered. The report is compiled, stored, and sent to the physician. Typically, the archived textual and graphic information related to each diagnostic code includes a report description, a report title, treatment options related to the diagnosis, protective measures related to the diagnosis, and frequently asked questions and answers related to the diagnosis. In addition, the relational database management system can be configured such that the entering of the diagnostic identifier code for the diagnosis automatically causes either the execution of a report compilation or the sending of the report to the physician by electronic data transmission. Commercially available relational database software programs contain a programming means for producing such a compilation. The actual programming can be done by one of ordinary skill in the art.

Preferably, the present invention includes entering a graphical or textual description of the sample analysis into the relational database. The database is configured such that when a report is compiled, this sample descriptive information is incorporated into the report. For example, the report would include a digitized graphic of a tissue sample showing diseased tissue and a description of the findings of a pathologist observing the tissue sample. Commercially available relational database software programs contain a programming means for producing such a compilation. The actual programming can be done by one of ordinary skill in the art.

In some instances, one might have archived textual and graphical information that is pertinent to more than one diagnostic code. In other words, the archived information suitable for inclusion and compilation in a report will be the same even if different diagnostic codes are entered. Here, the relational database can be modified to include a report type attribute, each report type being specific for a set of particular archived information. The relational database is modified also such that the diagnostic codes are entered as attributes for a report type. Commercially available relational database software programs contain a programming means for producing such a compilation The actual programming can be done by one of ordinary skill in the art.

The present invention also includes a memory storage device having stored thereon specific information related to the above method in a readable format, executable for query and report compilation by a relational database management system run on a computer. Such information includes a unique identifier code for a plurality of medical diagnoses that can be made from the analysis of a biological sample from a patient, each diagnostic identifier code being an attribute of a medical diagnosis; archival textual and graphic information as an attribute that is specific for each diagnostic identifier code; a unique identifier code for at least one patient as an attribute of the name of that patient; and a unique identifier code for at least one physician as an attribute of the name and address of the physician.

BEST MODES FOR CARRYING OUT THE INVENTION

Figure 1:
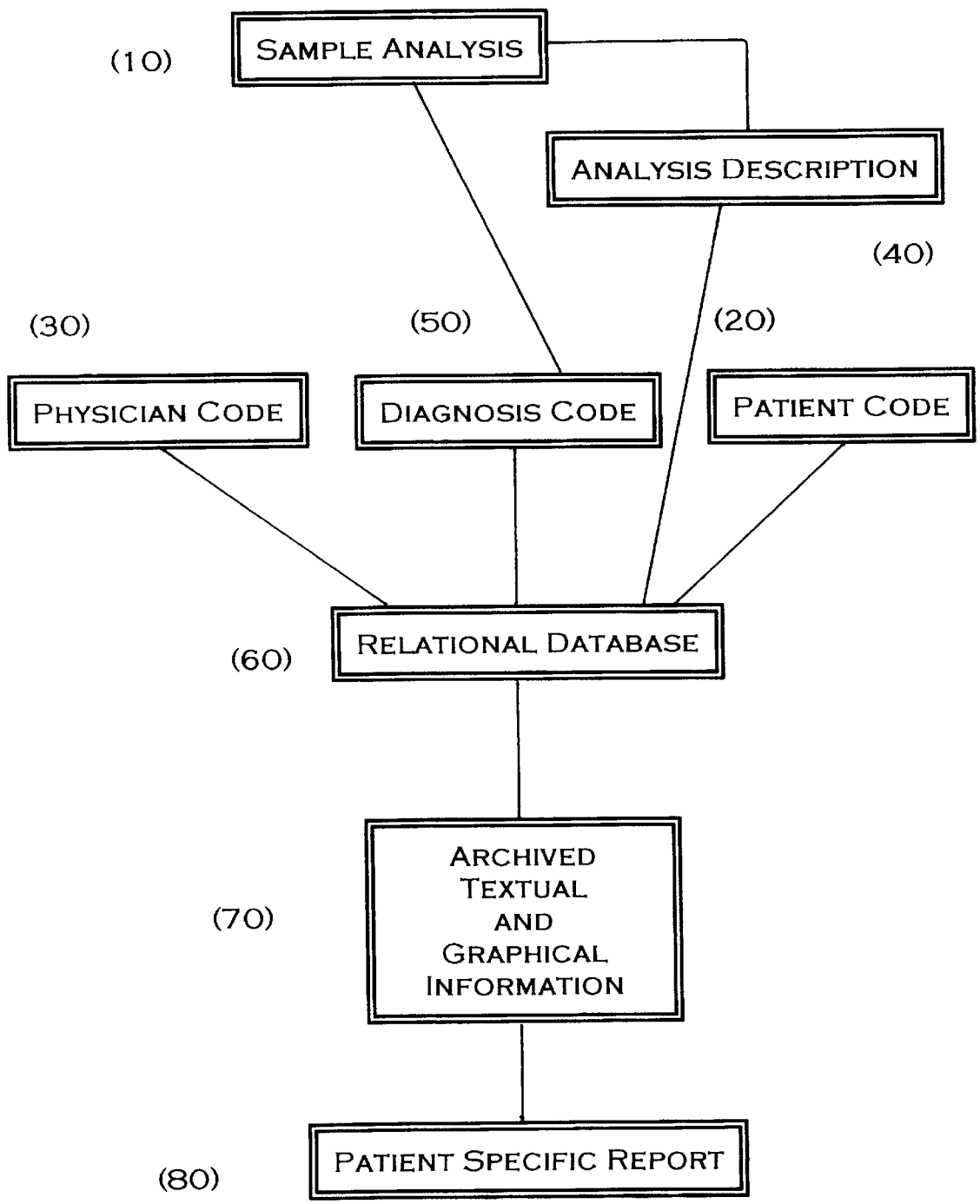
FIG. 1 is a schematic diagram of the flow of information into the relational database and the resulting patient specific report.
Figure 2:
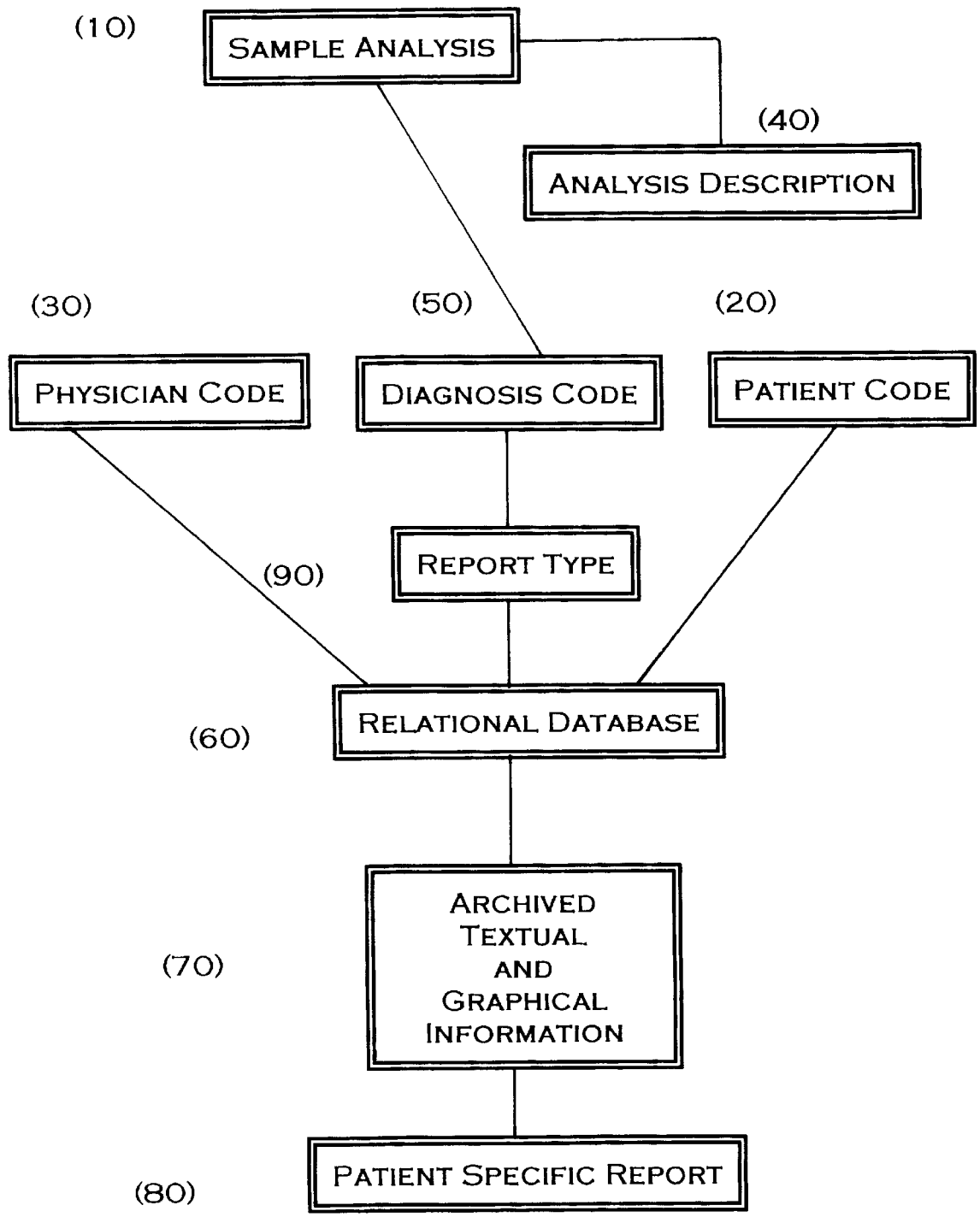
FIG. 2 is a schematic diagram of the flow of information into the relational database and the resulting patient specific report wherein a report type attribute is used.

A schematic representation of the present invention is shown in FIGS. 1 and 2. As an example, a sample analysis (10) is performed for a patient, such as a pathological examination of two biopsy samples taken from the lower esophagus of a patient. The pathologist diagnoses the uppermost specimen as being positive for low grade dysplasia and distinctive for a condition known as "Barrett's Esophagus", and the lower specimen also as being distinctive for Barrett's Esophagus. The specimens have already been assigned a unique patient identifier code (20) and a unique physician's code (30). The pathologist makes a written description (40) of their observation of the specimens, such as—"The metaplastic epithelium shows feature of low grade dysplasia. Nuclear abnormalities include stratification, crowding, and hyperchromasia." A photomicrograph of a slide section of one of the specimens is made and digitally scanned. The pathologist selects the already entered alphanumeric diagnostic code (50) which is unique in the relational database for Barrett's Esophagus.

The diagnostic code and the sample analysis description are entered into the relational database (60) through normal data input means for textual and graphical information. By entering the diagnostic code, a report query and compilation is automatically made. Archival textual and graphical information is selected (70) by the relational database which corresponds to Barrett's Esophagus. A patient specific medical counseling report (80) is generated by the relational database which contains the following information: an identification of the patient by name and birth date; the conclusion from the pathological examination, i.e., that the patient has Barrett's Esophagus; a reproduced image of the photomicrograph; a layman's description of Barrett's Esophagus, (which is a condition where the lining of the lower portion of the esophagus changes and grows to resemble cells that line either the stomach or the intestine); a description of the options for treating Barrett's Esophagus, including endoscopic monitoring and medications; a list of commonly asked questions and answers to those questions; a list of protective measures that can be taken, (such as avoiding alcohol and smoking); and a list of associations that can provide further information. All of this information, except the sample analysis description and photomicrograph came from archived information. The report is sent by modem transmission to a computer in the office of the physician of the patient, where it is printed out.

FIG. 2 represents an alternative embodiment where the relational database has been configured such that an entered diagnosis code (50) is an attribute of a report type (90).

In a preferred embodiment, the relational database needed to practice the present invention can be written or programmed from commercially available relational database software programs such as MicroSoft SQL Server, MicroSoft Access, or any other open database connectivity (OBDC) compliant program. Programming the relational database to be configured to perform in accordance with the present invention is within the skill of the ordinary software programmer. Suitable computer hardware include any microprocessing based system that can run such software. Obviously, data input means must be provided for entering all of the codes and information which are required by the present invention. Furthermore, data output means should be provided for delivering information to the patient or physician, typically by print or visual means. The actual graphical design of a particular report can be accomplished using a rapid application development tool such as Visual Basic.

In another preferred embodiment, the present invention can also generate a report that provides geographically local information that is useful to a patient or a physician of the patient. To customize the report for such local information, the relational database needs more information entered. A geographic identifier code is assigned to each physician. Typically, this can be based on a postal code such as the ZIP code. The geographic identifier code is entered into the relational database management system as an attribute of the address of the physician. Archival textual and graphical resource information is entered into the relational database management system which is based on local resources related to each entered diagnostic identifier code, and is related to the address of the physician. The relational database management system is configured further such that if a diagnostic identifier code is entered for the patient, then a report can be compiled that retrieves the resource archived textual and graphical information specific for the entered diagnostic code and the entered physician code, and discloses the local resources related to the diagnosis which are available to the patient. Commercially available relational database software programs contain programming means for producing such a relationship. The actual programming can be done by one of ordinary skill in the art.

In yet another preferred embodiment, the present invention can also generate a report that provides information that is useful to a physician of the patient. To customize the report for the physician or health care provider. Additional information must be entered into the relational database. Archival textual and graphical information based either on testimonial attributes of the physician or on physician specific treatment advice is entered into the relational database management system. This archival textual and graphic testimonial information is related to at least one of the entered diagnostic identifier codes and also to the physician identifier code. Examples of testimonial information include business cards, logos, advertising, and the like. The relational database management system is configured such that if a diagnostic code is entered for the patient, then a report can be compiled that retrieves and inserts into a report the testimonial archived textual and graphical information specific for the entered physician code, and discloses testimonial attributes of the physician to the patient. Commercially available relational database software programs contain programming means for producing such a result. The actual programming can be done by one of ordinary skill in the art.

Preferred embodiments of memory storage devices comprise a memory storage device, such as magnetic tape, magnetic hard drive disk, or an optical CD-ROM disk, having stored thereon a digitized report compiled from retrieved and inserted archived textual and graphical information that is specific for a unique diagnostic code selected as a result of an analysis of a biological sample from at least one patient. The stored report identifies the patient, discloses the results of the sample analysis, and addresses the report to the physician for that patient. These memory storage devices can include the archived textual and graphic information related to each diagnostic code that is compiled into the patient-specific report. Such information includes a report description, a report title, treatment options, protective measures, and frequently asked questions and answers.

Alternatively, the memory storage devices can include a stored report that contains a geographic identifier code which is as an attribute of the address of for each physician, and archival textual and graphical information based on local resources available to each patient which is an attribute of at least one of the entered diagnostic identifier codes and also to the address of the physician for each patient.

Additional preferred memory storage devices include a memory storage device, such as magnetic tape, magnetic hard drive disk, or an optical CD-ROM disk, having stored thereon a relational database software program which has been configured such that if a unique diagnostic identifier code which is an attribute of a specific medical diagnosis is entered as an attribute for an entered patient identifier code, then a report can be compiled that retrieves and inserts entered diagnostic archival textual and graphical information which is specific for the entered diagnostic code, and further identifies the patient. These devices also can contain a relational database configured so as to include in the compiled report any textual or graphical description of a sample analysis that has been entered as a separate attribute for a related diagnostic code and patient code.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for generating a document that contains medical information specific to a patient, the medical information resulting from an analysis of a biological sample from the patient comprising:

a) assigning a unique identifier code for a plurality of medical diagnoses that can be made from the analysis of the biological sample and entering, as an attribute for a specific medical diagnosis, each diagnostic identifier code into a relational database management system that is stored on a memory device and is executable on a computer for query and report compilation;

b) entering diagnostic archival textual and graphic information into the relational database management system as an attribute that is specific for and related to the underlying diagnosis associated with each diagnostic identifier code and that is explanatory to the patient with respect to that diagnosis;

c) assigning a unique identifier code for the patient and entering the patient identifier sequence in the relational database management system; as an attribute of the name of the patient;

d) assigning a unique identifier code for a physician for the patient and entering the physician identifier sequence in the relational database management system as an attribute of the name and address of the physician;

e) analyzing the biological sample from the patient whereby a diagnosis is made that has an entered diagnostic identifier code;

f) configuring the relational database management system such that if a diagnostic identifier code is entered as an attribute for an entered patient identifier code, then a report can be compiled that retrieves and inserts the explanatory diagnostic archival textual and graphical information specific for and related to the underlying diagnosis associated with the entered diagnostic code, and identifies the patient;

g) entering the diagnostic identifier code for the diagnosis into the relational database management system;

h) executing a report compilation by the relational database management system; and i) saving the compiled, patient-specific report.

2. The method of claim 1 wherein a textual or graphical description of the results of the sample analysis are entered into the relational database management system as a separate attribute for the related entered diagnosis code and entered patient code, the relational database being configured such that when a report is compiled, the textual or graphical sample result information is included in the report.

3. The method of claim 1 wherein the relational database management system is configured such that the entering of the diagnostic identifier code for the diagnosis automatically causes the execution of a report compilation.

4. The method of claim 2 wherein the relational database management system is configured such that the entering of the diagnostic identifier code for the diagnosis also automatically causes the addressing and sending of the report to the physician by electronic data transmission.

5. The method of claim 1 wherein the explanatory archived textual and graphic diagnostic information related to each diagnostic code includes a report description, a report title, treatment options related to the diagnosis, protective measures related to the diagnosis, and frequently asked questions and answers related to the diagnosis.

6. The method of claim 1 wherein the diagnosis is based on an examination of the biological sample by a pathologist.

7. The method of claim 1 wherein:

a) a geographic identifier code is assigned to each physician and entered into the relational database management system as an attribute of the address of the physician;

b) archival textual and graphical information is entered into the relational database management system which is based on local resources related to each entered diagnostic identifier code, the archival textual and graphic resource information being related to the address of the physician; and c) the relational database management system is configured such that if a diagnostic identifier code is entered for the patient, then a report can be compiled that retrieves the archived textual and graphical resource information specific for the entered diagnostic code and the entered physician code, and discloses the local resources related to the diagnosis which are available to the patient.

8. The method of claim 1 wherein:

a) archival textual and graphical information based on testimonial attributes of the physician is entered into the relational database management system, the testimonial archival textual and graphic information being related to the physician identifier code; and b) the relational database management system is configured such that if a diagnostic code is entered for the patient, then a report can be compiled that retrieves and inserts into a report the archived textual and graphical testimonial information specific for the entered physician code, and discloses testimonial attributes of the physician to the patient.

* * * * *